(12) United States Patent
Wang et al.

(10) Patent No.: US 12,004,956 B1
(45) Date of Patent: Jun. 11, 2024

(54) ACETABULAR RECONSTRUCTION PROSTHESIS WITH PILING-CUP SYSTEM

(71) Applicant: Jilin University, Changchun (CN)

(72) Inventors: Jincheng Wang, Changchun (CN); Xin Zhao, Changchun (CN); He Liu, Changchun (CN); Rongqi Zhou, Changchun (CN); Yue Lu, Changchun (CN)

(73) Assignee: Jilin University, Changchun (CN)

( * ) Notice: Subject to any disclaimer, the term of this patent is extended or adjusted under 35 U.S.C. 154(b) by 0 days.

(21) Appl. No.: 18/521,847

(22) Filed: Nov. 28, 2023

(30) Foreign Application Priority Data

Jun. 5, 2023 (CN) .......................... 202310653957.5

(51) Int. Cl.
    *A61F 2/34*     (2006.01)
    *A61B 17/86*     (2006.01)
    *A61F 2/30*     (2006.01)
    *A61F 2/46*     (2006.01)

(52) U.S. Cl.
CPC ............ *A61F 2/34* (2013.01); *A61B 17/8665* (2013.01); *A61F 2002/30433* (2013.01); *A61F 2002/30787* (2013.01); *A61F 2002/3092* (2013.01); *A61F 2002/30985* (2013.01); *A61F 2002/3401* (2013.01); *A61F 2002/4633* (2013.01); *A61F 2310/00023* (2013.01)

(58) Field of Classification Search
CPC .............. A61F 2/34; A61F 2002/30433; A61F 2002/3401
See application file for complete search history.

(56) References Cited

U.S. PATENT DOCUMENTS 5,013,313 A * 5/1991 Surer ........................ A61F 2/34
    606/328
2007/0129808 A1* 6/2007 Justin ...................... A61F 2/389
    623/22.36

FOREIGN PATENT DOCUMENTS

| CN | 107049559 A | * | 8/2017 | ............... A61F 2/32 |
| DE | 4133433 C1 | * | 5/1993 | ......... A61B 17/8066 |
| FR | 2827503 A1 | * | 1/2003 | ............... A61F 2/34 |

* cited by examiner

*Primary Examiner* — Javier G Blanco
(74) *Attorney, Agent, or Firm* — Stephen Y. Liu; Carstens, Allen & Gourley, LLP

(57) ABSTRACT

An acetabular reconstruction prosthesis with a piling-cup system is provided, which includes an iliac posterior pile screw, an iliac anterior pile screw, a pubic pile screw, an ischial pile screw, abutments, a 3D (three-dimensional) printed porous titanium mesh cup, locking screws, nuts, and tail cap screws. Four pile screws are the iliac posterior pile screw facing posterior of the ilium, the iliac anterior pile screw facing iliac tubercle, the ischial pile screw running along ischium ramus, and the pubic pile screw running along pubic ramus. A stable prothesis support system is formed in the acetabular reconstruction prosthesis with a piling-cup system, which conforms to the biomechanical characteristics of physiological pelvis, reduces the risk of prosthesis loosening and dislocation, and improves long-term stability of the prosthesis through biological fixation.

8 Claims, 5 Drawing Sheets

FIG. 5A
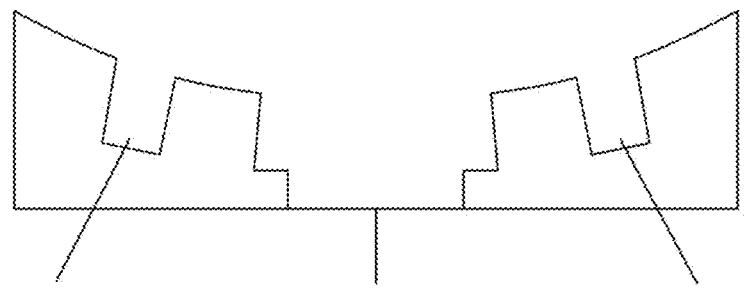
52  53  51  54  55
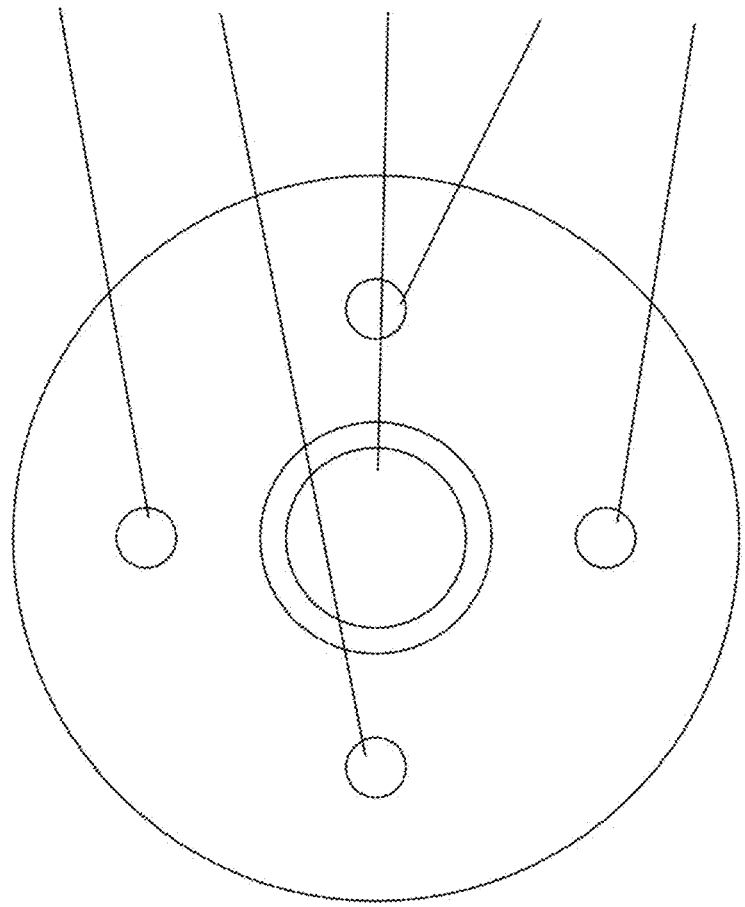
FIG. 5B

ACETABULAR RECONSTRUCTION PROSTHESIS WITH PILING-CUP SYSTEM

CROSS-REFERENCE TO RELATED APPLICATION

This patent application claims the benefit and priority of Chinese Patent Application No. 202310653957.5 filed with the China National Intellectual Property Administration on Jun. 5, 2023, the disclosure of which is incorporated by reference herein in its entirety as part of the present application.

TECHNICAL FIELD

The present disclosure relates to the technical field of medical devices, and in particular to an acetabular reconstruction prosthesis with a piling-cup system, which is applicable for acetabular artificial joint reconstruction.

BACKGROUND

With the continuous increase in the number of total hip arthroplasty (THA) surgeries, more and more patients need for hip joint revision and reconstruction. However, postoperative prosthesis failure often leads to different degrees of bone defects in revision surgery, which has certain damage to the stability and fixation of hip joint reconstruction prosthesis implants. At present, there are a variety of acetabular reconstruction prostheses in the clinic, such as jumbo-cup system, metal reinforcement rings, and custom triflange acetabular components, but these prostheses still have some problems. When the jumbo-cup system are used to reconstruct the acetabulum, displacement of the acetabular prosthesis may occur, which affects the stability and function of the prosthesis. The metal reinforcement rings will play a temporary fixation role during the fusion process between allogenic bone and host bone, but this may lead to fatigue fracture due to the lack of biological fixation. The custom triflange acetabular components require high prosthesis manufacturing cost, long prosthesis design time and are difficult to install during surgery.

In conclusion, the prosthesis implants used for hip joint revision and reconstruction at present have some problems, such as high surgical complexity and difficulty, decreased clinical postoperative stability and even prosthesis fracture. Therefore, it has become a focus and difficulty in orthopedic clinical research to develop an acetabular prosthesis which is easy to install during surgery and has good stability.

Based on the "three-column theory" of acetabulum, the applicant proposed a "four-column theory" comprising (1) an iliac posterior pile screw facing posterior of ilium, (2) an iliac anterior pile screw facing iliac tubercle, (3) an ischial pile screw running along ischium ramus, and (4) a pubic pile screw running along pubic ramus. According to the "four-column theory", the acetabular prosthesis can be fixed more stably, the mechanical loads borne by ilium can be effectively dispersed, and the wear rate and looseness rate of the acetabular prosthesis can be reduced, and thereby the fixation effect is improved.

After further improvement, on the basis of the "four-column theory" of screws, the "two-line four-column theory" was derived. The so-called two lines are a pubic ramus line and an ischii ramus line. It should be noted that the pubic pile screw and the iliac posterior pile screw are located in the same plane and intersect at the center of acetabulum, and the ischial pile screw and the iliac anterior pile screw are located in the same plane and intersect at the center of acetabulum.

Pile foundation is a common form of foundation, widely used in the field of civil engineering, and a new solution for acetabular reconstruction is provided by the high bearing capacity of pile foundation. Pile foundation comprises two parts: multiple piles (referred to as pile groups) buried in the foundation and a pile cap (referred to as a cushion cap) combining the pile groups to work together. Pile foundation can bear vertical loads, horizontal loads, uplift loads and vibration loads, and thus is the most widely used form of deep foundation. According to usage function, pile foundation can be divided into: (1) vertical compressive pile, that is mainly used to bear vertical downward loads; (2) vertical uplift pile, that is mainly used to bear vertical uplift loads; (3) horizontally loaded pile, that is mainly used to bear horizontal loads; and (4) composite loaded pile, that is mainly used to bear significant vertical and horizontal loads. In acetabular reconstruction surgery, pile screws, as a new pile foundation technology, are used to be implanted into bones to support prosthesis. The pile screws at different positions are used to bear different forms of loads. For example, the iliac posterior pile screw and the pubic pile screw are mainly used to bear vertical and horizontal loads, the iliac anterior pile screw is mainly used to bear vertical downward loads, and the ischial pile screw is mainly used to bear vertical uplift loads. Based on the disclosure, it is expected to provide a more stable and reliable support mode for acetabular reconstruction surgery, and the pile screws at different positions can bear different forms of loads, thus better adapting to different needs in acetabular reconstruction surgery, improving the stability of prosthesis, reducing the risk of prosthesis failure, and improving the rehabilitation effect and life quality of patients.

SUMMARY

Based on the defects of the current acetabular prosthesis, an acetabular reconstruction prosthesis with a piling-cup system is provided, which is mainly used for surgical treatment of acetabular bone defect reconstruction. By combining the basic anatomical structure of pelvis with the pile foundation, not only the surgical difficulty is reduced, but also the bearing capacity of the postoperative acetabular prosthesis is effectively improved, and the biomechanical stability of the prosthesis-bone interface in postoperative immediate and medium to long term is improved, thus reducing the risk of prosthesis failure.

To achieve the objective above, the present disclosure provides the following technical solution:

The present disclosure is inspired by the basic anatomical structure of pelvis and pile foundation.

When an acetabular reconstruction prosthesis with a piling-cup system was intended to be used, the applicant deeply analyzed the anatomical structure of pelvis and proposed the "two-line four-column theory". The two lines formed by the four columns bear the function of transferring horizontal and vertical loads in pelvis, respectively. Pile foundation comprises pile groups and a pile cap. The function of the pile foundation is to transfer the load to the deep soil layer with good bearing capacity, so as to meet the requirements of bearing capacity and settlement. Based on the anatomical structure of pelvis and the theoretical basis of pile foundation, an acetabular reconstruction prosthesis with a piling-cup system is provided, which includes an iliac posterior pile screw, an iliac anterior pile screw, a pubic pile screw, an ischial pile screw, abutments, a 3D (three-dimensional) printed porous titanium mesh cup, locking screws, nuts, and tail cap screws.

A pile seat of the iliac posterior pile screw, the iliac anterior pile screw, the pubic pile screw and the ischial pile screw is inserted into a central screw hole of a respective abutment of the abutments and fixed by a respective nut of the nuts, respectively.

The 3D-printed porous titanium mesh cup is fixed to the respective abutment by a respective tail cap screw of the tail cap screws, and fixation is reinforced by four locking screws around the respective tail cap screw.

The iliac posterior pile screw, the iliac anterior pile screw, the pubic pile screw and the ischial pile screw are implanted into an acetabular wall according to the anatomical structure of pelvis, wherein the iliac posterior pile screw faces posterior of the ilium, the iliac anterior pile screw faces iliac tubercle, the ischial pile screw runs along ischium ramus, and the pubic pile screw runs along pubic ramus.

The iliac posterior pile screw, the iliac anterior pile screw, the pubic pile screw and the ischial pile screw each include a main pile, a pile seat and a tail cap screw path.

The main pile is in a screw type to be screwed into the normal bone, and the main pile is divided into two types: an osseointegration pile and a bone cement pile.

Each abutment of the abutments is of a disc structure and is fixed to the pile seat with the respective nut, and the upper surface of each abutment completely fits the 3D-printed porous titanium mesh cup. A left screw hole, a front screw hole, a rear screw hole and a right screw hole for fixing the 3D-printed porous titanium mesh cup by the locking screws are formed around the central screw hole of each abutment.

The 3D-printed porous titanium mesh cup is of a porous network structure, which is fixed on the abutments by the tail cap screws, and fixation can be reinforced by the locking screws through the left screw hole, the front screw hole, the rear screw hole, and the right screw hole from all sides.

The porous network structure of the 3D-printed porous titanium mesh cup is a rough surface conducive to osseointegration.

The iliac posterior pile screw, the iliac anterior pile screw, the pubic pile screw, the ischial pile screw, the abutments, the 3D-printed porous titanium mesh cup, the locking screws, the nuts and the tail cap screws each are made of Ti-6A1-4V.

Compared with the current acetabular prosthesis, the present disclosure has the following beneficial effects:

(1) in the present disclosure, the pile screws are implanted based on the anatomical structure of pelvis, which conforms to the biomechanics characteristics of pelvis and is helpful to reduce the occurrence of postoperative complications such as prosthesis loosening and dislocation.

(2) in the present disclosure, the main pile of the pile screws is in a screw type, so as to be screwed into normal bone. According to the function, the main pile can be divided into two types: osseointegration pile (which is a coated screw and can be subjected to osseointegration with normal bone) and bone cement pile (mainly used for osteoporotic bone or after bone grafting). Different pile screws can be selected according to different degrees of bone defect.

(3) in the present disclosure, the pile screws and the 3D-printed porous titanium mesh cup form a pile foundation, so that the reconstructed acetabulum has higher bearing capacity, can bear both longitudinal and horizontal loads, and the stability of the acetabular reconstruction prosthesis is improved.

(4) in the design of the present disclosure, the acetabular reconstruction prosthesis with the pile foundation structure designed is fixed by a piling-cup system, which can improve the long-term stability of the acetabular reconstruction prosthesis.

(5) in the present disclosure, the 3D-printed porous titanium mesh cup has a porous network structure, and the porous network structure has a rough surface conducive to osseointegration, allowing for long-term prosthesis stability through biological fixation.

(6) the present disclosure proposes a perfect reconstruction concept and a complete reconstruction process, thus the acetabular reconstruction can be quickly and accurately completed, the surgical efficiency can be improved, and the postoperative rehabilitation of patients can be accelerated.

BRIEF DESCRIPTION OF THE DRAWINGS

FIG. 5A is a front view and FIG. 5B is a top view of an abutment according to the present disclosure;

Figure 1:
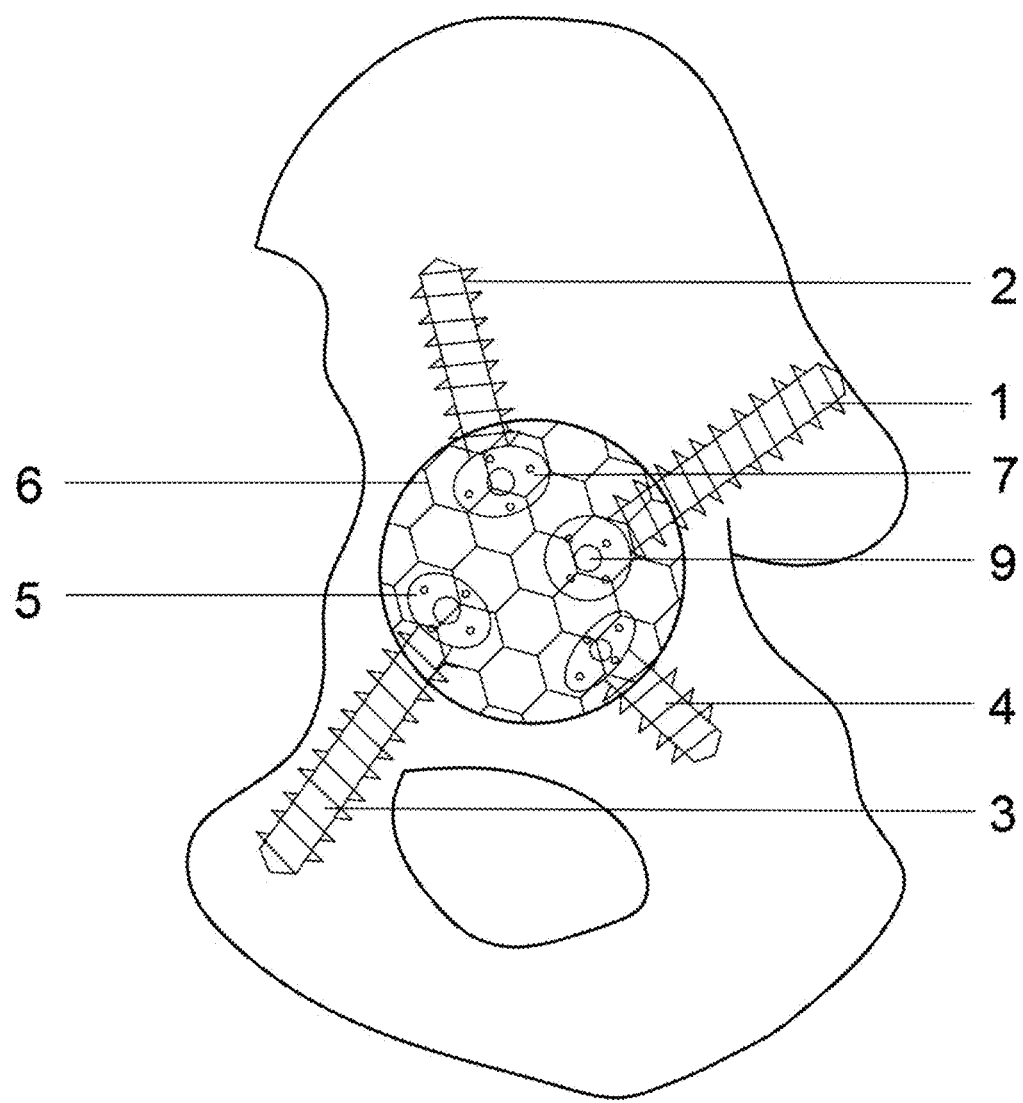
FIG. 1 is a schematic diagram of the overall structure of an acetabular reconstruction prosthesis with a piling-cup system according to the present disclosure.

In the drawings: 1—iliac posterior pile screw; 2—iliac anterior pile screw; 3—pubic pile screw; 4—ischial pile screw; 5—abutment; 6—3D-printed porous titanium mesh cup; 7—locking screw; 8—nut; 9—tail cap screw; 11—main pile; 12—pile seat; 13—tail cap screw path; 51—central screw hole; 52—left screw hole; 53—front screw hole; 54—rear screw hole; 55—right screw hole.

DETAILED DESCRIPTION OF THE EMBODIMENTS

Figure 2:
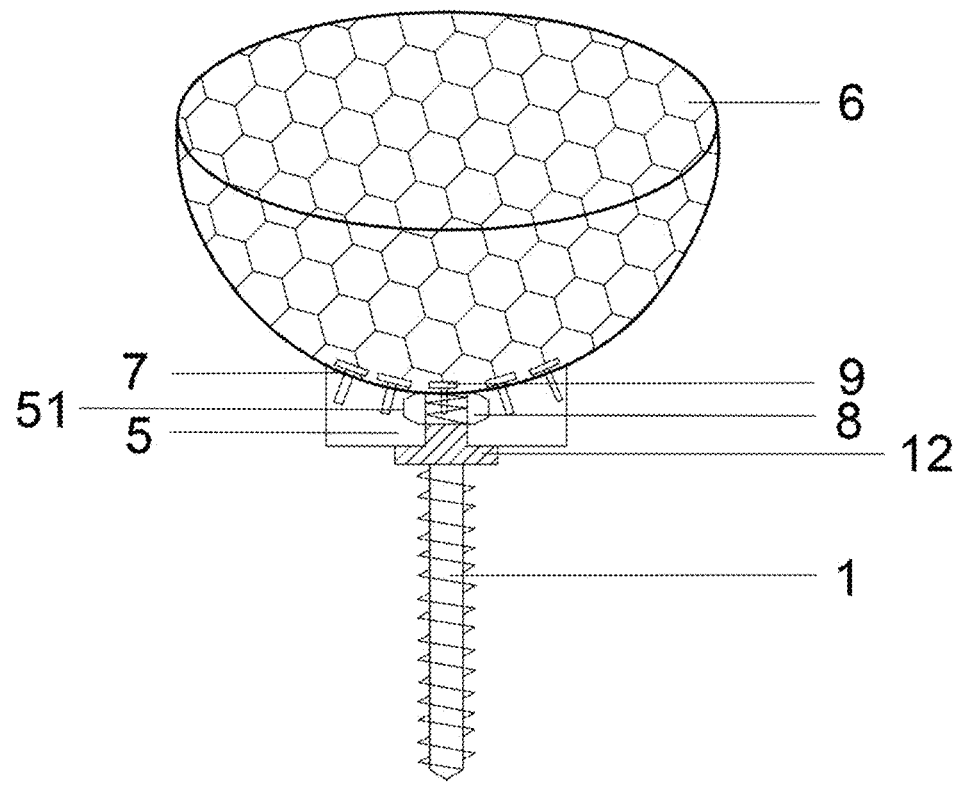
FIG. 2 is an installation schematic diagram of a pile screw and a 3D-printed porous titanium mesh cup according to the present disclosure.

As shown in FIGS. 1 and 2, the acetabular reconstruction prosthesis with a piling-cup system comprises an iliac posterior pile screw 1, an iliac anterior pile screw 2, a pubic pile screw 3, an ischial pile screw 4, abutments 5, a 3D-printed porous titanium mesh cup 6, locking screws 7, nuts 8, and tail cap screws 9. The iliac posterior pile screw 1, the iliac anterior pile screw 2, the pubic pile screw 3 and the ischial pile screw 4 are implanted into an acetabular wall according to the anatomical structure of pelvis, wherein the iliac posterior pile screw 1 faces posterior of the ilium, the iliac anterior pile screw 2 faces iliac tubercle, the pubic pile screw 3 runs along pubic ramus, and the ischial pile screw 4 runs along ischium ramus. The acetabular reconstruction prosthesis with a piling-cup system can achieve the mechanical fixation between the prosthesis and acetabular bone, thus preventing the prosthesis from displacing while providing initial postoperative mechanical stability.

As shown in FIG. 2, a pile seat 12 of a pile screw is inserted into a central screw hole 51 of a respective abutment 5 and fixed with a respective nut 8. The 3D-printed porous titanium mesh cup 6 is fixed to the abutment 5 by a respective tail cap screw 9, and fixation is reinforced by four locking screws 7 around the respective tail cap screw 9. The overall stability of the prosthesis is improved through the screw-nut locking fixation between the components, and the prosthesis is effectively prevented from displacing.

Figure 3:
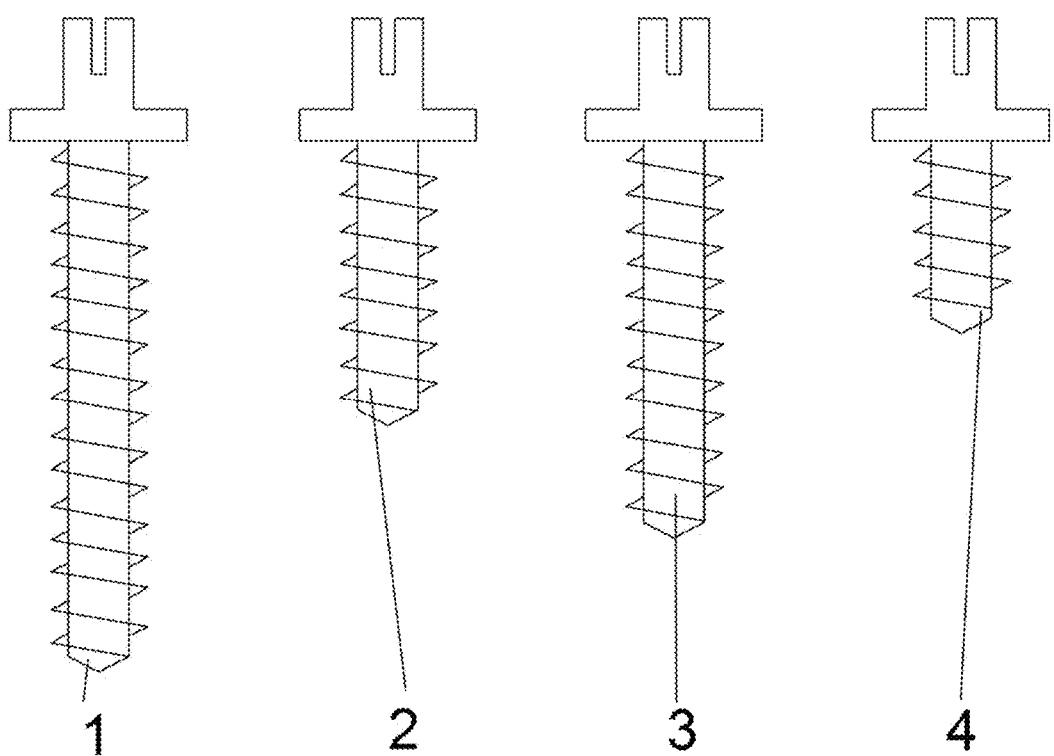
FIG. 3 is a schematic diagram showing comparison of the specifications of four pile screws according to the present disclosure.

As shown in FIG. 3, in this embodiment, the length of the iliac posterior pile screw 1 is 70 mm-100 mm, preferably 75 mm-85 mm.

The length of the iliac anterior pile screw 2 is 30 mm-50 mm, preferably 35 mm-45 mm.

The length of the pubic pile screw 3 is 50 mm-70 mm, preferably 55 mm-65 mm.

The length of the ischial pile screw 4 is 25 mm-45 mm, preferably 30 mm-35 mm.

The diameter of each of the iliac posterior pile screw 1, the iliac anterior pile screw 2, the pubic pile screw 3 and the ischial pile screw 4 is 6.5 mm-9 mm, preferably 7 mm-8 mm. The pile screws with this specification can allow the prothesis to bear larger loads in different directions and improve the stability of the prosthesis, so as to prevent the prosthesis from displacing due to excessive loads.

Figure 4:
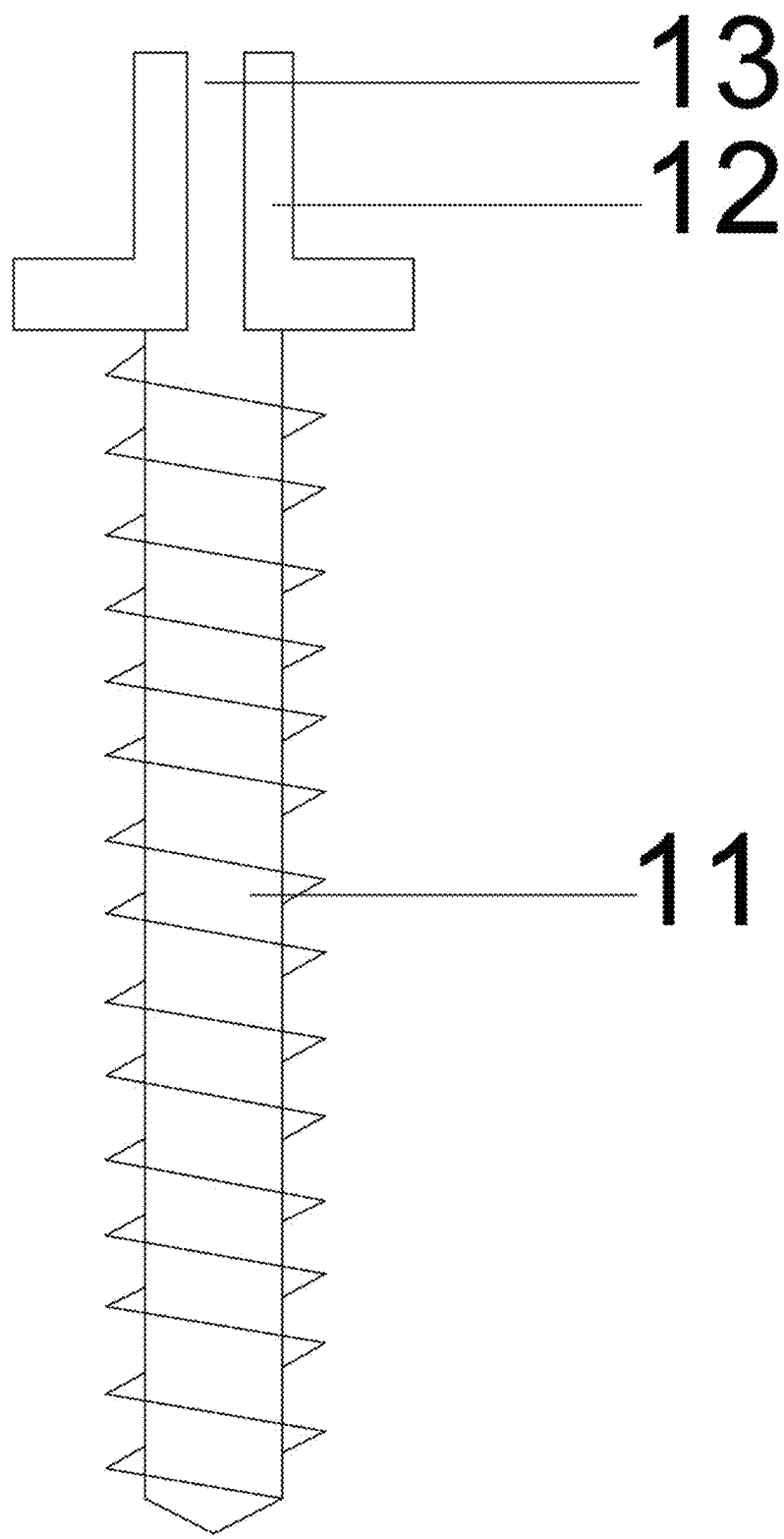
FIG. 4 is a structural schematic diagram of a pile screw according to the present disclosure.

As shown in FIG. 4, the iliac posterior pile screw 1, the iliac anterior pile screw 2, the pubic pile screw 3, and the ischial pile screw 4 are of the same structure. Taking the iliac posterior pile screw 1 as an example, the iliac posterior pile screw basically includes a main pile 11, a pile seat 12, and a tail cap screw path 13. The main pile 11 is in a screw type to be screwed into normal bone. According to the function, the main pile can be divided into two types: an osseointegration pile (which is a coated screw and can be subjected to osseointegration with normal bone) and a bone cement pile (mainly used for osteoporotic bone or after bone grafting). Different pile screws can be selected according to different degrees of bone defect degrees. The pile seat 12 is used for bearing the respective abutment 5 and is fixed to the respective abutment 5 by the respective nut 8. By such a design, different degrees of bone defects are taken into consideration, and good stability of prosthesis-bone interface can be obtained after the prosthesis reconstruction.

As shown in FIGS. 5A and 5B, each abutment 5 is of a disc structure and is provided with a central screw hole 51 at the center, and the center screw hole 51 is used for fixing the abutment 5 to the pile seat 12 by the respective nut 8. An upper surface of each abutment 5 completely fits the 3D-printed porous titanium mesh cup 6. A left screw hole 52, a front screw hole 53, a rear screw hole 54 and a right screw hole 55 for fixing the 3D-printed porous titanium mesh cup 6 by the locking screws 7 are formed around the central screw hole 51 of each abutment 5.

The iliac posterior pile screw 1, the iliac anterior pile screw 2, the pubic pile screw 3, the ischial pile screw 4, the abutments 5, the 3D-printed porous titanium mesh cup 6, the locking screws 7, the nuts 8 and the tail cap screws 9 each are made of Ti-6A1-4V.

Figure 6:
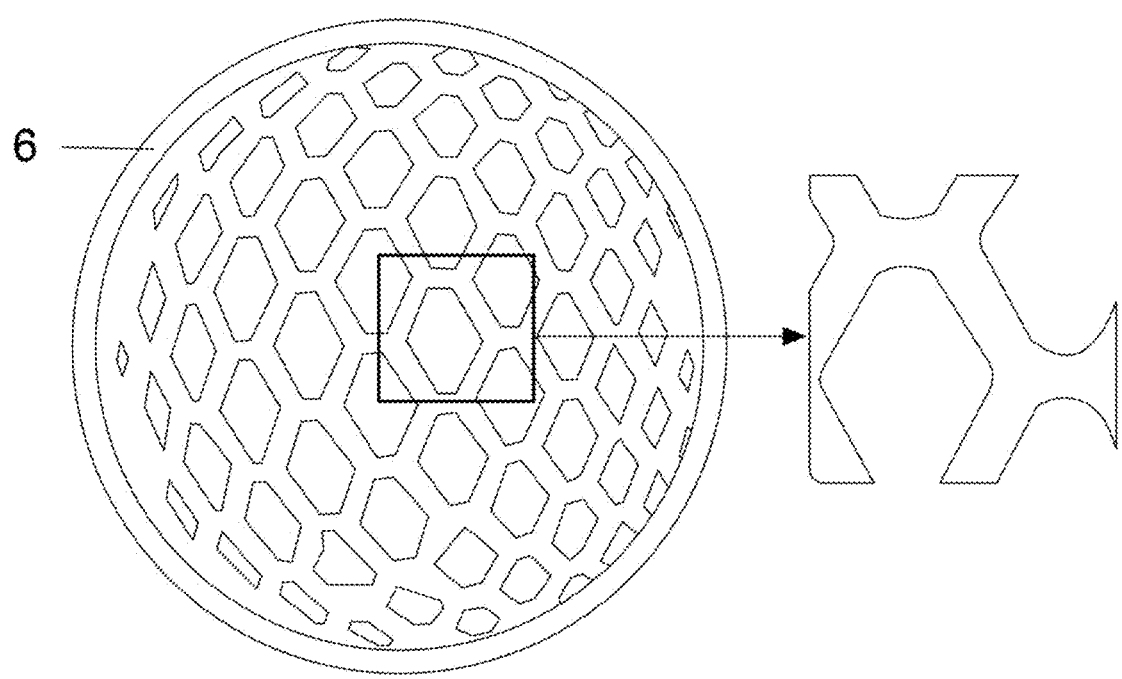
FIG. 6 is a top view of a 3D-printed porous titanium mesh cup according to the present disclosure.

As shown in FIG. 6, the 3D-printed porous titanium mesh cup 6 is of a porous network structure, and can be fixed to the upper surface of the abutments 5 by the locking screws 7 through the left screw hole 52, the front screw hole 53, the rear screw hole 54, and the right screw hole 55. Meanwhile, the porous network structure of the 3D-printed porous titanium mesh cup 6 is a rough surface conducive to osseointegration, and the fixation of a pile surface structure and the overall stability of the prosthesis are improved.

The dimensions of the four pile screws in the acetabular reconstruction prosthesis with a piling-cup system of this embodiment are measured by the following steps:

Step one: collecting CT data of pelvis of a patient, and importing the CT data into Mimics software;

Step two: reconstructing a personalized 3D model of pelvis of the patient in the Mimics software based on the CT data;

Step three: importing the personalized 3D model into Magics software in STL (Standard Template Library) file format for model trimming; and Step four: simulating the pile screws with cylinders and conducting a simulated implantation by Magics software, so as to design the dimensions of the pile screws within the safety area of the patient.

What is claimed is:

1. An acetabular reconstruction prosthesis with a piling-cup system, comprising an iliac posterior pile screw (1), an iliac anterior pile screw (2), a pubic pile screw (3), an ischial pile screw (4), abutments (5), a 3D-printed porous titanium mesh acetabular cup (6), locking screws (7), nuts (8), and tail cap screws (9);

the iliac posterior pile screw (1), the iliac anterior pile screw (2), the pubic pile screw (3), the ischial pile screw (4) are sized and configured to be implanted into an acetabular wall according to anatomical structure of pelvis, wherein the iliac posterior pile screw (1) faces posterior of ilium, the iliac anterior pile screw (2) faces iliac tubercle, the ischial pile screw (4) is sized and configured to run along ischium ramus, and the pubic pile screw (3) is sized and configured to run along pubic ramus;

a pile seat (12) of the ischial pile screw (4) is inserted into a central screw hole (51) of a respective abutment (5) of the abutments (5) and fixed by a respective nut (8) of the nuts (8), respectively;

wherein each abutment (5) of the abutments (5) is disc-shaped and is fixed to the pile seat (12) by the respective nut (8), and an upper surface of each abutment (5) completely fits an outside surface of the 3D-printed porous titanium mesh acetabular cup (6);

wherein a left screw hole (52), a front screw hole (53), a rear screw hole (54) and a right screw hole (55) for fixing the 3D-printed porous titanium mesh acetabular cup (6) by the locking screws (7) are formed around the central screw hole (51) of each abutment (5);

wherein the 3D-printed porous titanium mesh acetabular cup (6) is fixed to the respective abutment (5) by a respective tail cap screw (9) of the tail cap screws (9), and fixation is reinforced by four locking screws (7) around the respective tail cap screw (9).

2. The acetabular reconstruction prosthesis with a piling-cup system according to claim 1, wherein a length of the iliac posterior pile screw (1) is 70 mm-100 mm;

a length of the iliac anterior pile screw (2) is 30 mm-50 mm;

a length of the pubic pile screw (3) is 50 mm-70 mm;

a length of the ischial pile screw (4) is 25 mm-45 mm;

a diameter of each of the iliac posterior pile screw (1), the iliac anterior pile screw (2), the pubic pile screw (3), the ischial pile screw (4) is 6.5 mm-9 mm.

3. The acetabular reconstruction prosthesis with a piling-cup system according to claim 2, wherein dimensions of the iliac posterior pile screw (1), the iliac anterior pile screw (2), the pubic pile screw (3) and the ischial pile screw (4) are obtained through simulated implantation measurement in Magics software.

4. The acetabular reconstruction prosthesis with a piling-cup system according to claim 1, wherein the iliac posterior pile screw (1), the iliac anterior pile screw (2), the pubic pile screw (3), the ischial pile screw (4) each comprise a main pile (11), a pile seat (12), and a tail cap screw path (13).

5. The acetabular reconstruction prosthesis with a piling-cup system according to claim 4, wherein the main pile (11) is in a screw type to be screwed into normal bone, and the main pile (11) is divided into two types: an osseointegration pile and a bone cement pile.

6. The acetabular reconstruction prosthesis with a piling-cup system according to claim 1, wherein the 3D-printed porous titanium mesh cup (6) is of a porous network structure and is fixed on the abutments (5) by the tail cap screws (9), and fixation is randomly reinforced by the locking screws (7) through the left screw hole (52), the front screw hole (53), the rear screw hole (54), and the right screw hole (55) from all sides.

7. The acetabular reconstruction prosthesis with a piling-cup system according to claim 1, wherein a porous network structure of the 3D-printed porous titanium mesh cup (6) is a rough surface conducive to osseointegration.

8. The acetabular reconstruction prosthesis with a piling-cup system according to claim 1, wherein the iliac posterior pile screw (1), the iliac anterior pile screw (2), the pubic pile screw (3), the ischial pile screw (4), the abutments (5), the 3D-printed porous titanium mesh cup (6), the locking screws (7), the nuts (8) and the tail cap screws (9) each are made of Ti-6A1-4V.

\* \* \* \* \*